United States Patent [19]

Beck et al.

[11] Patent Number: 5,386,051

[45] Date of Patent: Jan. 31, 1995

[54] PROCESS FOR THE PREPARATION OF 1,2,3-TRICYANOBENZENE, PHTHALOCYANINES WHICH ARE OBTAINABLE FROM 1,2,3-TRICYANOBENZENE, AND THEIR USE AS PIGMENTS

[75] Inventors: Gunther Beck; Bernd Kaletta, both of Leverkusen, Germany

[73] Assignee: Bayer Aktiengesellschaft, Leverkusen, Germany

[21] Appl. No.: 166,329

[22] Filed: Dec. 10, 1993

Related U.S. Application Data

[63] Continuation of Ser. No. 971,029, Nov. 3, 1992, abandoned.

[30] Foreign Application Priority Data

Nov. 13, 1991 [DE] Germany ............... 4137270

[51] Int. Cl.$^6$ .................................. C07C 253/14
[52] U.S. Cl. .................................. 558/343
[58] Field of Search ................. 540/143; 558/343

[56] References Cited

U.S. PATENT DOCUMENTS

| | | | |
|---|---|---|---|
| 2,182,763 | 3/1937 | Muehlbauer | 540/122 |
| 2,647,908 | 2/1950 | Buc | 540/135 |
| 3,492,308 | 1/1970 | Brach et al. | 540/143 |
| 3,998,839 | 12/1976 | Seha | 540/122 |
| 4,719,286 | 1/1988 | Matlow | 528/362 |
| 4,946,762 | 8/1990 | Albert et al. | 430/270 |
| 4,959,487 | 9/1990 | Yamasaki et al. | 558/343 |
| 5,175,336 | 12/1992 | Beck et al. | 558/343 |
| 5,187,295 | 2/1993 | Schach | 558/343 |

FOREIGN PATENT DOCUMENTS

| | | |
|---|---|---|
| 0272565 | 6/1988 | European Pat. Off. |
| 0459196 | 12/1991 | European Pat. Off. |
| 0337209 | 10/1989 | Japan ............... 540/143 |

OTHER PUBLICATIONS

John H. Gorvin, "Hydroxydenitration by a Nef-type Process . . . " J.C.S. Chem. Comm. 1976, pp. 972–973.
Witulski et al., "Über die Addition von Cyanacetylen . . . ", Chem. Ber. 123 (1990), pp. 2015–2022.
Ferris et al, "Photochemical Cycloaddition Reactions of Cyanoacetylene . . . ", J. Org. Chem. 1990, V. 55, pp. 5601–5606.
108:23341z, Ehashi et al, "Phthalocyanines"; Chem. Abstr. V. 108, (1988), p. 77.

*Primary Examiner*—Mukund J. Shah
*Assistant Examiner*—Pavanaram K. Spipada
*Attorney, Agent, or Firm*—Sprung Horn Kramer & Woods

[57] ABSTRACT

1,2,3-Tricyanobenzene can be prepared in a good yield from fluorobenzonitriles by reaction with an alkali metal cyanide. This product can be converted into metal-free tetracyanophthalocyanines or into the corresponding metal complexes by tetramerisation, if appropriate in the presence of metals or metal compounds. These products are excellent organic pigments.

1 Claim, No Drawings

PROCESS FOR THE PREPARATION OF 1,2,3-TRICYANOBENZENE, PHTHALOCYANINES WHICH ARE OBTAINABLE FROM 1,2,3-TRICYANOBENZENE, AND THEIR USE AS PIGMENTS

This application is a continuation of application Ser. No. 07/971,029, filed Nov. 3, 1992 abandoned.

The invention relates to a process for the preparation of 1,2,3-tricyanobenzene from fluorobenzonitriles by reaction with alkali metal cyanides, tetracyanophthalocyanines which are obtainable from 1,2,3-tricyanobenzene, and the use of these phthalocyanines as coloured pigments.

1,2,3-Tricyanobenzene and various processes for its preparation are known. According to J. Chem. Soc., Chem. Commun. 972 (1976) in the reaction of 1,3-dicyano-2-nitrobenzene with potassium cyanide in dimethylsulphoxide or dimethylformamide at 100° C., a reaction mixture is formed which is said to comprise, in addition to 65–75% of 2,6-dicyanophenol and about 10% of a black resinous material, about 15% of 1,2,3-tricyanobenzene. The publication mentioned contains no further experimental data at all.

In the reaction of cyanoacetylene with [2,2]-paracyclophane at 160° C., a 1:4 mixture of 1,2,3- and 1,2,4-tricyanobenzene was isolated as a by-product in a 15% yield (corresponding to a yield of 3% of 1,2,3-tricyanobenzene, based on the cyanoacetylene); Chem. Ber. 123 (1990), 2015.

According to J. Org. Chem. 55 (1990), 5601, it is also possible to prepare 1,2,3-tricyanobenzene from 1,2,3-benzenetricarboxylic acid (obtainable, for example, by potassium permanganate degradation of naphthalic anhydride) in a 3-stage reaction via the acid chloride and the acid amide in a total yield of just about 12% of theory is also possible.

The object of the invention was therefore, inter alia, to provide a simple and economical process for the preparation of 1,2,3-tricyanobenzene.

Surprisingly, it has been found that 1,2,3-tricyanobenzene is accessible in a good yield by reaction of fluorocyanobenzenes with an alkali metal cyanide.

The invention therefore relates to a process for the preparation of 1,2,3-tricyanobenzene by reaction of compounds of the formula

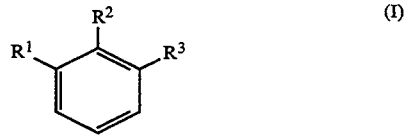

(I)

wherein $R^1$, $R^2$ and $R^3$
independently of one another denote F or CN, with the proviso that at least 1 F and at least 1 CN radical are present,
with an alkali metal cyanide.

The starting compounds (I) comprise 2,3- and 2,6-difluorobenzonitrile, 1,2-dicyano-3-fluorobenzene and 1,3-dicyano-2-fluorobenzene. The preferred starting substance is 2,6-difluorobenzonitrile, which is prepared on an industrial scale.

The alkali metal cyanides used are preferably the cyanides of sodium or potassium.

The process according to the invention is preferably carried out in organic diluents; suitable such diluents are, in particular, aprotic dipolar organic solvents, for example N,N-di-$C_1$-$C_4$-alkylamides of aliphatic $C_1$-$C_6$-carboxylic acids, such as N,N-dimethylformamide, N,N-diethylformamide, N-methylpyrrolidinone and N-methylcaprolactam; aliphatic sulphoxides, such as dimethyl sulphoxide, aliphatic sulphones, such as dimethyl sulphone and tetramethylene sulphone; and furthermore tetramethylurea, N,N'-dimethyl-1,3-imidazolidin-2-one and hexamethylphosphoric acid trisamide. N,N-Dimethylformamide and N-methylpyrrolidinone are particularly preferred.

The amount of diluent is in general chosen such that 1 to 100, preferably 5 to 20 ml of diluent are employed per gram of starting substance (I).

Formally, one mol of alkali metal cyanide is required for complete reaction of one mol of dicyanofluorobenzene, and 2 mol of alkali metal cyanide are required for reaction of one mol of difluorobenzonitrile. However, it may be advantageous to use less than the equivalent amount of alkali metal cyanide, or to interrupt the reaction prematurely, because the unreacted starting substances, in particular the 2,6-difluorobenzonitrile, can be separated off from the reaction mixture particularly easily on the basis of their higher volatility. As a rule, 50 to 120, preferably 50 to 100, in particular 50 to 99 mol % of alkali metal cyanide will be employed per equivalent of fluoride.

The process according to the invention can be carried out at temperatures of $-50°$ C. to $+100°$ C., preferably from $-20°$ C. to $+60°$ C., particularly preferably from $0°$ C. to $+30°$ C. mild conditions largely avoiding the formation of undesirable products.

The reaction is in general carried out under normal pressure.

The process according to the invention is preferably carried out by adding the alkali metal cyanide to a solution of the starting substance (I) in an anhydrous solvent, with exclusion of moisture and while stirring, and subsequently stirring the mixture vigorously, for example, for 10 to 100 hours. When the reaction has ended (or has been interrupted prematurely), the reaction mixture is then added to excess (for example 2 to 10 times the volume) ice-water. It is also possible to strip off all or some of the solvent before the reaction mixture is stirred into water, any residual amount of unreacted alkali metal cyanide present first advantageously being removed by filtration. The 1,2,3-tricyanobenzene precipitated on stirring with water is isolated by filtration and if appropriate subsequently purified, for example by vacuum sublimation and/or recrystallisation.

It has furthermore been found that 1,2,3-tricyanobenzene is outstandingly suitable as a starting material for the preparation of new tetracyano-phthalocyanines and metal complexes thereof.

The invention thus furthermore relates to compounds of the formula

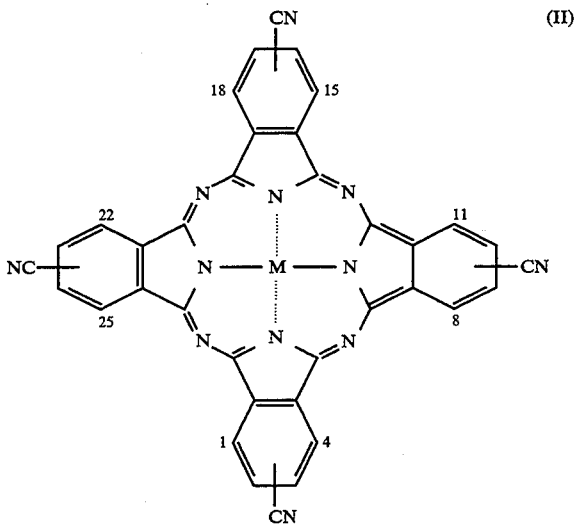

wherein the nitrile groups are in each case in one of the two possible o-positions ("o-position" being understood as meaning the 1-, 4-, 8-, 11-, 15-, 18-, 22- and 25-positions in the phthalocyanine II) and M denotes 2 hydrogen atoms, magnesium, calcium, copper, iron, cobalt, nickel, zinc, tin, vanadium-oxy, titanium-oxy, chromium-oxy or manganese.

The phthalocyanines (II) can be prepared by processes analogous to known processes, such as are described, for example in K. Venkataraman, "The Chemistry of Synthetic Dyes", Volume II, Academic Press, Inc., New York, 1952, pages 1118–1142,
or N. M. Bigelow and M. A. Perkins in Lubs (editor), "The Chemistry of Synthetic Dyes and Pigments", Reinhold Publishing Corp., New York, 1955, pages 577–606, and in the literature quoted therein. The metal complexes (II) can thus be prepared, for example, 1) by direct reaction of 1,2,3-tricyanobenzene with metals or metal salts, oxides or hydroxides, if appropriate in the presence of bases, 2) by addition of metals onto metal-free phthalocyanines (II), and 3) by metal exchange with other metallophthalocyanines (II) under suitable conditions. Metal-free phthalocyanines (II) are accessible 1) by direct tetramerisation of 1,2,3-tricyanobenzene in the presence of bases, and 2) by removal of the central atom from the corresponding metallophthalocyanines (II). The preparation does not have to, but can be carried out. in inert organic solvents.

Suitable metal salts, oxides and hydroxides for the preparation of the metal complexes (II) include, for example, magnesium chloride, bromide, acetate, oxide and hydroxide, calcium chloride and acetate, copper(I) chloride, bromide and cyanide, copper(II) chloride, acetate and nitrate, iron(II) chloride, iron(III) chloride and nitrate, cobalt chloride, bromide and acetate, nickel chloride, bromide, acetate and oxide, zinc chloride and acetate, tin chloride and acetate, vanadium(III) and -(IV) chloride, vandium(V) oxychloride, titanium(III) and -(IV) chloride, chromium(III) chloride, fluoride and oxide and manganese(II) chloride and acetate.

They are as a rule employed in amounts of 0.5 to 10, preferably 1 to 2 mol per mol of metal-free phthalocyanine (II).

Suitable bases for the preparation of the metal-free and metal-containing phthalocyanines (II) include, for example, tertiary amines, such as 1,4-diazobicyclo[2.2.2]octane, 1,8-diazabicyclo[5.4.0]-undec-7-ene, 1,5-diazabicyclo[4.3.0]-non-5-ene, the sodium, potassium and lithium alcoholates of monohydric $C_1$-$C_{12}$-alcohols, such as methanol, ethanol, isopropanol, butanol, pentanol and the like, or of dihydric $C_2$-$C_{12}$-alcohols, such as ethylene glycol, and others.

Suitable organic solvents for the preparation of the phthalocyanines (II) are, for example, the abovementioned alcohols themselves, aprotic dipolar organic solvents, for example N,N-di-$C_1$-$C_4$-alkylamides of aliphatic $C_1$-$C_6$-carboxylic acids, such as N,N-dimethylformamide, N,N-diethylformamide, N-methylpyrrolidinone and N-methylcaprolactam; aliphatic sulphoxides, such as dimethyl sulphoxide, aliphatic sulphones, such as dimethyl sulphone and tetramethylene sulphone; and furthermore tetramethylurea, N,N'-dimethyl-1,3-imidazolidin-2-one and hexamethylphosphoric acid trisamide.

They are in general employed in amounts of 1 to 50, preferably 5 to 20% by weight, based on the sum of the starting components.

The preparation can be carried out at temperatures from 100 to 300, preferably 120° to 200° C. The reaction has ended when no further educt is detectable in the thin layer chromatogram.

The tetracyanophthalocyanines (II) according to the invention can be used for the preparation of very fast pigmented systems, such as mixtures with other substances, formulations, paints, printing inks, coloured paper and coloured macromolecular substances. Mixtures with other substances can be understood as meaning, for example, those with inorganic white pigments, such as titanium dioxide (rutlie). Formulations are, for example, flush pastes with organic liquids and, if appropriate, preservatives. The term paints represents, for example, physically or oxidatively drying coatings, stoving enamels, reactive coatings, two-component coatings, emulsion paints for weatherproof coatings and distempers. Printing inks are to be understood as meaning those for paper, textile and tin printing. The phthalocyanines (II) according to the invention are particularly suitable for pigmenting macromolecular organic substances.

The macromolecular substances can be of natural origin, such as rubber, obtained by chemical modification, such as acetylcellulose, cellulose butyrate or viscose, or produced synthetically, such as polymers, polyaddition products and polycondensates. Substances which may be mentioned are thermoplastic polymers, such as polyvinyl chloride, polyvinyl acetate, polyvinyl propionate, high molecular weight polyamides, polymers and copolymers of acrylic esters and/or methacrylic esters, acrylamide, butadiene and styrene, and polyurethanes and polycarbonates. The substances pigmented with the phthalocyanines (II) according to the invention can be in any desired form.

Because of their high transparency and fastness to weathering, the phthalocyanines (II) according to the invention are particularly suitable for use in car paints, in particular for metallic coatings. They can also be used as laser dyestuffs.

The phthalocyanines (II) according to the invention have excellent fastness to water, fastness to oil, fastness to acid, fastness to lime, fastness to alkali, fastness to solvents, fastness to overpainting, fastness to overspraying, fastness to sublimation, resistance to heat and resistance to vulcanisation, have a very high tinctorial strength, can easily be processed in plastic compositions, and in particular have an excellent fastness to weathering, light and migration.

Finally, the invention thus furthermore relates to the use of the phthalocyanines (II) as coloured pigments.

The percentage data of the following examples relate to the weight; parts are parts by weight.

EXAMPLE 1

Preparation of 1,2,3-tricyanobenzene 79.4 g (1.62 mol) of sodium cyanide are added to a solution of 150 g (1.08 mol) of 2,6-difluorobenzonitrile in 1500 ml of dry dimethylformamide at room temperature, while stirring and with exclusion of moisture. The reaction mixture is stirred vigorously at room temperature for 24 hours.

It is then poured into 7.5 l of ice-water, while stirring. The precipitate formed is then filtered off, washed with water and dried to constant weight. The crude product (108.5 g) is subsequently sublimed under about 0.1 mbar up to a bath temperature of 200° C. Yield: 100.5 g of 1,2,3-tricyanobenzene, corresponding to 81.1% of theory, based on the sodium cyanide, which is employed in less than the equivalent amount. Melting point: 177°-178° C. (from toluene or 1,2-dichloroethane).

IR (KBr): 3097, 3078, 3072, 2241, 1580, 1459, 1243, 828, 738 [cm$^{-1}$].

EXAMPLE 2

Preparation of tetracyanophthalocyanine 15.3 parts of 1,2,3-tricyanobenzene are dissolved in 150 parts of amyl alcohol. 9 parts of a 30% strength sodium methylate solution in methanol are then added, and the mixture is heated under reflux for 15 hours. The disodium salt formed is filtered off cold, with suction, and taken up in 100 parts of dimethylformamide, and 20 parts of acetic acid are added. The mixture is subsequently stirred at room temperature for 1 hour; the pigment is filtered off with suction, washed with methanol and dried in a drying cabinet at 50° C. 12.8 g of petrol-coloured tetracyanophthalocyanine are obtained.

EXAMPLE 3

Preparation of Cu tetracyanophthalocyanine 18 parts of 1,2,3-tricyanobenzene, 6 parts of copper-(II) acetate monohydrate and 500 parts of N-methylpyrrolidone are stirred at 100° C. for 1 hour; the mixture is then heated under reflux for 15 hours. The product is filtered off cold, with suction, washed with methanol and dried in a drying cabinet at 50° C. 16.2 g of blue copper tetracyanophthalocyanine are obtained. One of the conceivable structures is:

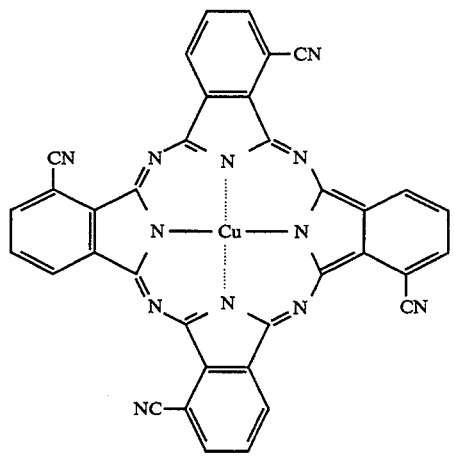

EXAMPLES 4-7

Preparation of other metallo-tetracyanophthalocyanines

Using the corresponding metal acetates or metal chlorides, the corresponding metal complexes (II) having the meaning for M and the associated colour shades mentioned in the table, are obtained by the process described in Example 3:

| Example | M = | Colour shade |
| --- | --- | --- |
| 4 | Ni | turquoise |
| 5 | Co | blue |
| 6 | Ti=O | blue |
| 7 | V=O | blue |

Use 1

Pigmented stoving enamelling 8 g of finely ground powder according to Example 2 are dispersed in 92 g of a stoving enamel having the following composition:
33% of alkyd resin
15% of melamine/formaldehyde resin
5% of glycol monomethyl ether
34% of xylene
13% of butanol Products based on synthetic and vegetable fatty acids, such as coconut oil, castor oil, dehydrated castor oil, linseed oil and others, are suitable alkyd resins. Urea/formaldehyde resins can be used instead of melamine/formaldehyde resins.

After the dispersion has taken place, the pigmented enamel is applied to films of paper, glass, plastic or metal and stoved at 130° C. for 30 minutes. The enamellings have a very good resistance to light and weathering and a good fastness to overpainting.

Use 2

Pigmented thermoplastics 0.2 g of pigment according to Example 2 is mixed with 100 g of polyethylene granules, polypropylene granules or polystyrene granules. The mixture can either be injection moulded directly in an injection moulding machine at 220° to 280° C., or processed to coloured bars in an extruder or to coloured hides on mixing rolls. If appropriate, the bars or hides are granulated, and injection moulded in an injection moulding machine.

The blue-green mouldings have a very good fastness to light and migration. Synthetic polyamides of caprolactam or of adipic acid and hexamethylenediamine or polyethylene terephthalate can be coloured in a similar manner at 280°–300° C., if appropriate under a nitrogen atmosphere.

Use 3

Pigmented printing ink

Using a printing ink prepared by grinding 35 g of pigment according to Example 2 and 65 g of linseed oil, and addition of 1 g of siccative (Co naphthenate, 50% strength in test benzine), blue-green offset prints of high brilliance and good depth of colour and very good fastness to light and coating are obtained. The use of this printing ink in letterpress, phototype, lithographic or steel engraving printing leads to blue-green prints having similar fastness properties. If the pigment is used for colouring in tin printing or gravure printing or low-viscosity printing inks, blue-green prints of similar fastness properties are obtained.

We claim:

1. Process for the preparation of 1,2,3-tricyanobenzene by reaction of compounds of the formula

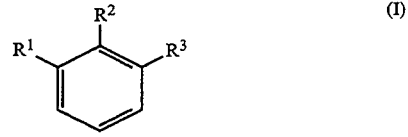

wherein $R^1$, $R^2$ and $R^3$
independently of one another denote F or CN, with the proviso that at least 1 F and at least 1 CN radical are present,
with an alkali metal cyanide.

* * * * *